(12) United States Patent
Alsharif et al.

(10) Patent No.: US 11,381,588 B2
(45) Date of Patent: Jul. 5, 2022

(54) CYBERSECURITY VULNERABILITY CLASSIFICATION AND REMEDIATION BASED ON INSTALLATION BASE

(71) Applicant: Saudi Arabian Oil Company, Dhahran (SA)

(72) Inventors: Sultan Saadaldean Alsharif, Khobar (SA); Wael Mohammed Alagi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 188 days.

(21) Appl. No.: 16/525,899

(22) Filed: Jul. 30, 2019

(65) Prior Publication Data

US 2021/0037038 A1  Feb. 4, 2021

(51) Int. Cl.
| | | |
|---|---|---|
| *H04L 9/40* | (2022.01) | |
| *G06F 17/16* | (2006.01) | |
| *G06F 21/55* | (2013.01) | |

(52) U.S. Cl.
CPC .......... *H04L 63/1433* (2013.01); *G06F 17/16* (2013.01); *G06F 21/554* (2013.01); *H04L 63/1441* (2013.01)

(58) Field of Classification Search
CPC . H04L 63/1433; H04L 63/1441; H04L 63/14; G06F 17/16; G06F 21/554;
(Continued)

(56) References Cited

U.S. PATENT DOCUMENTS 7,284,274 B1  10/2007  Walls et al.
8,392,997 B2   3/2013  Chen et al.
(Continued)

FOREIGN PATENT DOCUMENTS

KR       101692155       1/2017

OTHER PUBLICATIONS

Common Vulnerability Scoring System SIG. FIRST—Forum of Incident Response and Security Teams, www.first.org/cvss/.
(Continued)

*Primary Examiner* — Meng Li
(74) *Attorney, Agent, or Firm* — Leason Ellis LLP

(57) ABSTRACT

A system, a method, and a computer program for remediating a cyberattack risk for a computing resource located at a node in a computer network having a plurality of nodes. The solution includes receiving vulnerability score data that has a severity level for a vulnerability in the computing resource at the node, receiving a number of installations value ($N_{CRi}$) that indicates a number of instances the computing resource is included in the plurality of nodes, determining a percentile of occurrence value ($PO_{CRi}$) for the computing resource based on the number of installations value ($N_{CRi}$), applying a severity adjustment matrix to the severity level to determine a true severity level for the vulnerability in the computing resource, reprioritized the vulnerability in the computing resource based on the true severity level, and mitigating the cyberattack risk for the computing resource based on the true severity level.

16 Claims, 9 Drawing Sheets

300C

| $CR_i$ | Vulnerability | Vulnerability score | Severity Level |
|---|---|---|---|
| Word | CVE-42556 | 7.5 | High |
| Photoshop | CVE-54889 | 7 | High |
| Acrobat | CVE-63578 | 6 | Medium |
| CutPro | CVE-56894 | 5 | Medium |
| iExplore | CVE-94546 | 2 | Low |

(58) Field of Classification Search
CPC ...... G06F 21/577; G06F 21/55; H04W 12/71; H04W 12/12; A61B 2017/00119; A61B 2017/00123; A61B 2017/00128; A61B 2017/00221; A61B 2034/105; A61B 2034/107; A61B 2034/108; A61B 2034/2046; A61B 2034/2051; A61B 2034/2055; A61B 2034/2061; A61B 2034/2065; A61B 2034/252; A61B 2034/254; A61B 2034/256; A61B 2090/064; A61B 2090/364; A61B 2090/365; A61B 2090/368; A61B 2090/371; A61B 2090/3937; A61B 2090/3945; A61B 2090/397; A61B 2090/3983; A61B 2090/502; A61B 2090/508; A61B 34/20; A61B 34/25; A61B 34/30; A61B 34/76; A61B 90/36; A61B 90/50; A61B 90/94; A61B 90/96; A61B 90/98; A61B 34/10; A61B 17/17

See application file for complete search history.

(56) References Cited

U.S. PATENT DOCUMENTS

| | | | |
|---|---|---|---|
| 8,510,842 | B2 | 8/2013 | Amit et al. |
| 8,806,648 | B2 | 8/2014 | Guy et al. |
| 9,985,983 | B2 | 5/2018 | Seiver et al. |
| 10,162,970 | B2 | 12/2018 | Olson et al. |
| 10,305,925 | B2 | 5/2019 | Roytman et al. |
| 2004/0088565 | A1 | 5/2004 | Norman et al. |
| 2005/0132206 | A1 | 6/2005 | Palliyil et al. |
| 2014/0137257 | A1* | 5/2014 | Martinez ............. H04L 63/1433 726/25 |
| 2016/0065598 | A1* | 3/2016 | Modi ................... G06F 16/285 726/23 |
| 2017/0046519 | A1* | 2/2017 | Cam ..................... G06N 7/005 |
| 2017/0061132 | A1* | 3/2017 | Hovor ................ H04L 63/1433 |
| 2017/0078322 | A1 | 3/2017 | Seiver et al. |
| 2019/0050562 | A1* | 2/2019 | Rhee ................... G06F 16/9024 |

OTHER PUBLICATIONS

Robert Dell'Immagine. "How Does Vulnerability Scanning Work?" Qualys Community, Nov. 28, 2018, community.qualys.com/docs/DOC-1068-how-does-vulnerability-scanning-work.

"National Vulnerability Database ." NIST, nvd.nist.gov/vuln-metrics/cvss.

Ahmed, Mohammad Salim, et al. "Objective risk evaluation for automated security management." Journal of Network and Systems Management 19.3 (2011): 343-366.

International Search Report and Written Opinion in Corresponding PCT Application PCT/US2020/042334 dated Feb. 22, 2021. 12 pages.

International Preliminary Report on Patentability in corresponding PCT Application No. PCT/US2020/042334, dated Feb. 10, 2022; 7 pages.

* cited by examiner

300A

| CR$_i$ | Vulnerability |
|---|---|
| Word | CVE-42556 |
| Photoshop | CVE-54889 |
| Acrobat | CVE-63578 |
| CutPro | CVE-56894 |
| iExplore | CVE-94546 |

| Vulnerability score | Severity Level |
|---|---|
| 7.5 | High |
| 7 | High |
| 6 | Medium |
| 5 | Medium |
| 2 | Low |

FIG. 5

| CR_i | Vulnerability | Vulnerability score | Severity Level |
|---|---|---|---|
| Word | CVE-42556 | 7.5 | High |
| Photoshop | CVE-54889 | 7 | High |
| Acrobat | CVE-63578 | 6 | Medium |
| CutPro | CVE-56894 | 5 | Medium |
| iExplore | CVE-94546 | 2 | Low |

| $CR_i$ | Vulnerability | Vulnerability Score | Severity Level | $N_{CR_i}$ |
|---|---|---|---|---|
| Word | CVE-42556 | 7.5 | High | 50,000 |
| Photoshop | CVE-54889 | 7 | High | 3,000 |
| Acrobat | CVE-63578 | 6 | Medium | 30,000 |
| CutPro | CVE-56894 | 5 | Medium | 1,000 |
| iExplore | CVE-94546 | 2 | Low | 45,000 |

| Percentile | Severity Quantifier |
|---|---|
| 80% – 100% | Critical |
| 50% - 80% | High |
| 10% - 50% | Medium |
| 1% - 10% | Low |

| | 80% – 100% | 50% - 80% | 10% - 50% | 1% - 10% |
|---|---|---|---|---|
| Critical | Critical | Critical | Critical | Critical |
| High | Critical ↑ | High | High | High |
| Medium | Critical ↑ | High ↑ | Medium | Medium |
| Low | Critical ↑ | High ↑ | Medium ↑ | Low |

FIG. 9

| $CR_i$ | $N_{CR_i}$ | Percentage | Severity Level | True Severity Level |
|---|---|---|---|---|
| Word | 50,000 | 91% | High | Critical |
| Photoshop | 3,000 | 5.45% | High | High |
| Acrobat | 30,000 | 91% | Medium | High |
| CutPro | 1,000 | 1.81% | Medium | Medium |
| iExplore | 45,000 | 81.81% | Low | Critical |

CYBERSECURITY VULNERABILITY CLASSIFICATION AND REMEDIATION BASED ON INSTALLATION BASE

FIELD OF THE DISCLOSURE

The present disclosure relates to a system, a method, and a computer program for detecting, identifying, assessing or remediating security vulnerabilities in a network system, and, more particularly, for detecting, identifying, assessing, or remediating vulnerabilities in computing resources or groups of computing resources in a network system.

BACKGROUND OF THE DISCLOSURE

A cybersecurity flaw is often referred to in the industry as a vulnerability, and it is defined in the ISO/IEC 27002 information security standard as "a weakness of an asset or group of assets that can be exploited by one or more threats." The ISO/IEC 27002 standard is published by the International Organization for Standardization (ISO) and the International Electrotechnical Commission (IEC). An asset can include a computing resource such as, for example, any software, firmware or hardware, or any device that has an Internet Protocol (IP) address, including, for example, a router, a switch, a server, a printer, a scanner, a storage device, a computing device, or a communicating device. A non-limiting example of a system that is commonly employed to identify and assess principal characteristics of vulnerabilities in computing resources is the Common Vulnerability Scoring System (CVSS), which was the result of research carried out by the National Infrastructure Advisory Council (NIAC).

The CVSS is a free and open industry standard for assessing the severity of vulnerabilities in computing resources. CVSS produces and assigns numerical scores to vulnerabilities in computing resources. Scores are typically between 0 and 10, with 10 being representative of the most critical vulnerabilities. Its quantitative model ensures repeatable accurate measurement while enabling visibility into the underlying vulnerability characteristics that were used to generate the scores. These scores can be used to calculate the risks associated with the vulnerabilities, as well as to prioritize remediation efforts.

While assessment tools like CVSS can be helpful in building cybersecurity remediation plans for prioritizing and remediating vulnerabilities in computer networks, such tools can be inadequate for computer networks that comprise large numbers of nodes. There exists an urgent unfulfilled need for a network security solution that can effectively and efficiently identify and prioritize vulnerabilities in computing resources for remediation in computer networks having large numbers of nodes.

SUMMARY OF THE DISCLOSURE

The disclosure provides a novel technology solution, including a method, a system, and a computer program for detecting, identifying, assessing, classifying or prioritizing vulnerabilities for remediation in computing resources in a network system.

According to another non-limiting embodiment of the disclosure, a method is provided for remediating a cyberattack risk for a computing resource located at a node in a computer network having a plurality of nodes. The method comprises: receiving vulnerability score data that includes a severity level for a vulnerability in the computing resource at said node; receiving a number of installations value ($N_{CRi}$) that indicates a number of instances the computing resource is included in the plurality of nodes; determining a percentile of occurrence value ($PO_{CRi}$) for the computing resource based on the number of installations value ($N_{CRi}$); applying a severity adjustment matrix to the severity level to determine a true severity level for the vulnerability in the computing resource; reprioritized the vulnerability in the computing resource based on the true severity level; and mitigating the cyberattack risk for the computing resource based on the true severity level.

The vulnerability score data can comprise a Common Vulnerability Scoring System (CVSS) score for the vulnerability in the computing resource.

The computing resource can comprise a software application.

The step of generating the remediation plan can comprise generating a weighted vulnerability classification summary matrix that includes the vulnerability in the computing resource.

The method can further include generating a remediation plan for the computer network.

The step of determining the percentile of occurrence value ($PO_{CRi}$) for the computing resource can be calculated based on the number of installations value ($N_{CRi}$) according to the equation $$PO_{CRi} = (N_{CRi}/n) \times 100$$

where n is the total number of nodes in the computer network.

The true severity level can comprise a critical rating when the percentile of occurrence value ($PO_{CRi}$) for the computing resource is determined to be in a top percentile group.

The method can further comprise generating a weighted vulnerability classification summary matrix that includes the vulnerability in the computing resource, and transmitting the weighted vulnerability classification summary matrix to a communicating device in the computer network.

The step off mitigating the cyberattack risk for the computing resource based on the true severity level can be executed by the communicating device.

According to another non-limiting embodiment of the disclosure, a non-transitory computer readable medium is provided that stores instructions for remediating a cyberattack risk in a computing resource located at a node in a computer network having a plurality of nodes. The non-transitory computer readable medium comprises machine executable code which when executed by at least one computing device, causes the at least one computing device to perform steps comprising: receiving vulnerability score data that includes a severity level for a vulnerability in the computing resource at said node; receiving a number of installations value ($N_{CRi}$) that indicates a number of instances the computing resource is included in the plurality of nodes; determining a percentile of occurrence value ($PO_{CRi}$) for the computing resource based on the number of installations value ($N_{CRi}$); applying a severity adjustment matrix to the severity level to determine a true severity level for the vulnerability in the computing resource; reprioritized the vulnerability in the computing resource based on the true severity level; and mitigating the cyberattack risk for the computing resource based on the true severity level. The vulnerability score data can comprise a CVSS score for the vulnerability in the computing resource. The computing resource can include a software application.

The machine executable code can further cause the at least one computing device to perform generating a remediation plan for the computer network.

The machine executable code can further cause the at least one computing device to generate a weighted vulnerability classification summary matrix that includes the vulnerability in the computing resource.

The percentile of occurrence value ($PO_{CRi}$) for the computing resource can be calculated based on the number of installations value ($N_{CRi}$) according to the equation $$PO_{CRi}=(N_{CRi}/n)\times 100$$

where n is the total number of nodes in the computer network. The true severity level can include a critical rating when the percentile of occurrence value ($PO_{CRi}$) for the computing resource is determined to be in a top percentile group.

According to another non-limiting embodiment of the disclosure, a cybersecurity risk remediation system is provided for remediating a vulnerability in a computing resource located at a node in a computer network having a plurality of nodes. The system comprises: an installation base determiner that calculates a percentile of occurrence value ($PO_{CRi}$) for the computing resource based on a number of installations value ($N_{CRi}$) that indicates a number of instances the computing resource is included in the plurality of nodes; a classification and prioritization unit that applies a severity adjustment matrix to a severity level of the vulnerability in the computing resource to determine a true severity level of the vulnerability in the computing resource; and a vulnerability remediation unit that transmits the true severity level to a communicating device in the computer network to mitigate the vulnerability in the computing resource based on the true severity level. The severity level can be based on a CVSS score for the vulnerability in the computing resource. The classification and prioritization unit can generate a weighted vulnerability classification summary matrix that includes the vulnerability in the computing resource.

The installation base determiner can calculate the percentile of occurrence value ($PO_{CRi}$) for the computing resource based on the number of installations value ($N_{CRi}$) according to the equation $$PO_{CRi}=(N_{CRi}/n)\times 100$$

where n is the total number of nodes in the computer network.

Additional features, advantages, and embodiments of the disclosure may be set forth or apparent from consideration of the detailed description and drawings. Moreover, it is to be understood that the foregoing summary of the disclosure and the following detailed description and drawings provide non-limiting examples that are intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced.

FIG. 4 shows an example of a vulnerability scanning summary matrix that can be generated or populated by the CVR.

FIG. 5 shows an example of a vulnerability score summary matrix that can be generated or populated by the CVR.

FIG. 6 shows an example of a vulnerability classification matrix that can be generated or populated by the CVR.

FIG. 7 shows an example of a vulnerability-installation-base (VIB) classification summary matrix that can be generated or populated by the CVR.

FIG. 8 shows an example of a severity quantifier matrix that can be generated or populated by the CVR.

FIG. 9 shows an example of a severity adjustment matrix that can be generated or populated by the CVR.

FIG. 10 shows an example of a weighted vulnerability classification summary matrix that can be generated or populated by the CVR.

Figure 1:
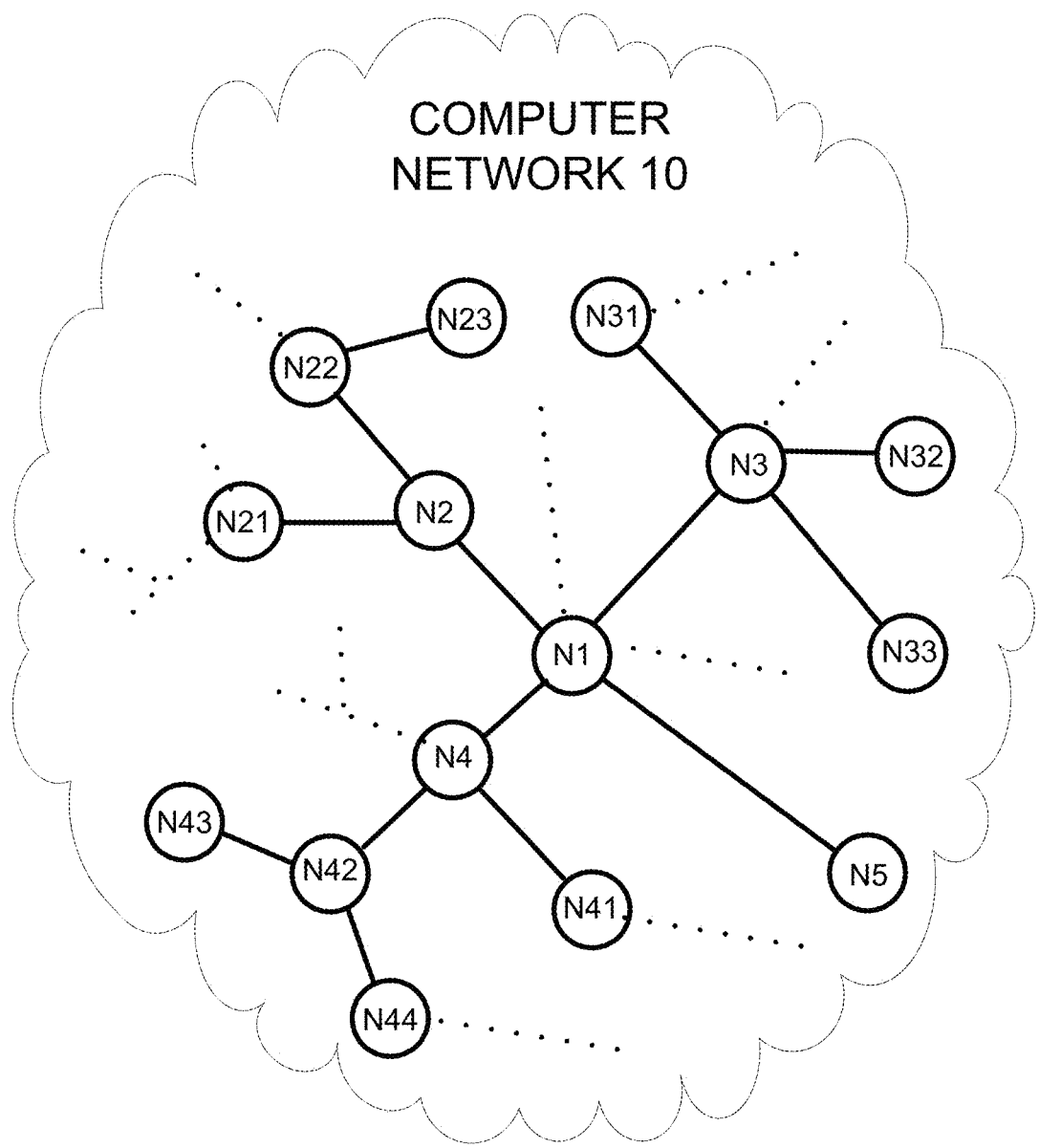
FIG. 1 shows a block diagram of an example of a computer network having many nodes.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described or illustrated in the accompanying drawings and detailed in the following description. It should be noted that features illustrated in the drawings are not necessarily drawn to scale, and features of one embodiment can be employed with other embodiments as those skilled in the art would recognize, even if not explicitly stated. Descriptions of well-known components and processing techniques may be omitted so as to not unnecessarily obscure the embodiments of the disclosure. The examples are intended merely to facilitate an understanding of ways in which the disclosure can be practiced and to further enable those skilled in the art to practice the embodiments of the disclosure. Accordingly, the examples and embodiments should not be construed as limiting the scope of the disclosure. Moreover, it is noted that like reference numerals represent similar parts throughout the several views of the drawings.

FIG. 1 shows a non-limiting embodiment of a computer network 10 having a plurality of nodes N1, N2, N21, N22, N23, N3, N31, N32, N33, N4, N41, N42, N43, N44, and N5 (collectively or individually referred to as a node "N"). The computer network 10 can include, for example, tens, hundreds, thousands, millions, billions, or more nodes N, any of which can include one or more computing resources. Each node N can include a location identifier that can identify the node's physical or virtual address in the computer network 10. The node location identifier can include, for example an Internet Protocol (IP) address, a Media Access Control (MAC) address, an Ethernet Hardware Address (EHA), hardware address, adapter address, physical address, or virtual address. Each node N can include one or more computing resources.

A computing resource can include one or more security vulnerabilities. The computer network 10 can include a network security solution constructed according to the principles of the disclosure. The network security solution can be located at one or more nodes N in the computer network 10, or the network security solution can be located outside of the computer network 10.

The network security solution can discover and identify security vulnerabilities in computing resources at nodes N in the computer network 10, such as, for example, servers, workstations or communicating devices located at nodes N. Alternatively (or additionally), the network solution can be provided with a list of all vulnerabilities in computing resources at nodes N in the computer network 10.

The network security solution can provide a list of vulnerabilities found at the nodes N in the computer network 10. The vulnerabilities can be classified and prioritized based on a vulnerability scoring system such as, for example, CVSS, or any compliance-oriented scheme appropriate for the computer network 10. The vulnerability scoring system can generate numerical scores that can be translated into a qualitative representation (for example, low, medium, high, or critical) to facilitate proper assessment and prioritization of vulnerability management processes for remediation of the vulnerabilities in the computer network 10. A remediation plan and timetable can be built for the vulnerabilities, and the vulnerabilities can be prioritized for remediation based on an installation base for the computer network 10.

Since it can be challenging to generate a remediation plan and timetable, or to prioritize remediation of vulnerabilities in a computer network 10 that has, for example, thousands of computing resources and millions of associated security weaknesses, the network security solution can include installation base determination that can provide installation base information for the computing resources in the computer network 10, which can be used to classify or reclassify, or prioritize or reprioritize vulnerabilities for remediation at the nodes N. Installation base information can include computing resource installation base information such as, for example, end-user software installation base information for each node N.

The installation base determination can be based on vulnerability scanning data or software development tool data that can be used to determine the computing resource installation base information for each node N in the computer network 10. The computing resource installation base information can be combined with a classification scheme, such as, for example, CVSS, to formulate a prioritized remediation plan and contextually classify and prioritize remediation activities based on the number of installations of a particular computing resource in the computer network 10.

The computer network 10 can include a private network, a private enterprise network, an enterprise network, a corporate network, a hospital network, a university network, a campus network, a military network, or a government network. The network security solution can include a network security system 100.

Figure 2:
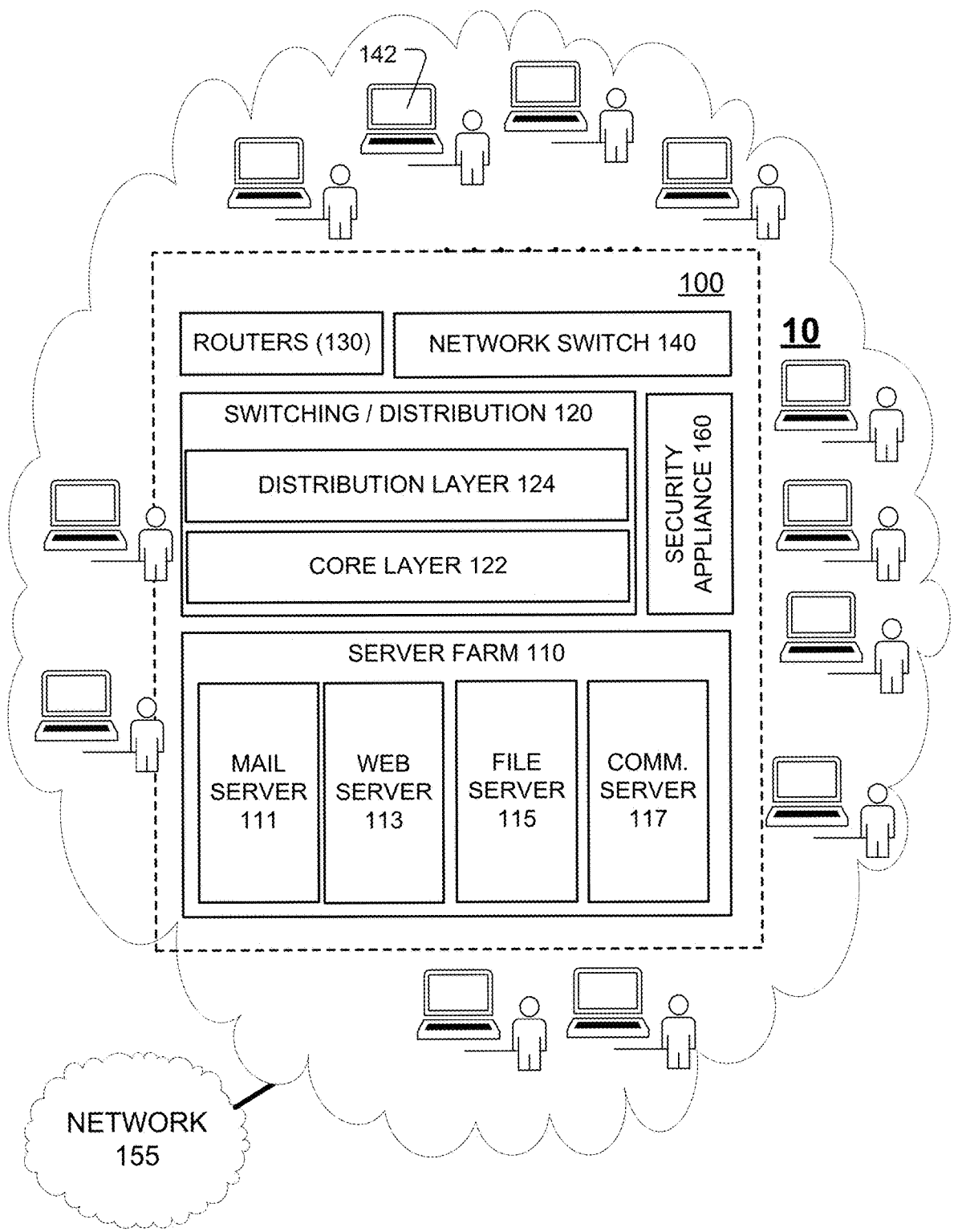
FIG. 2 shows an example of the computer network in FIG. 1 provided with a network security solution according to the principles of the disclosure.

FIG. 2 shows the computer network 10 comprising an embodiment of the network security system 100. As seen in FIG. 2, the computer network 10 can include a plurality of communicating devices 142 dispersed throughout the network, each of which can be located at a unique node N. Each communicating device 142 can include a location identifier, such as, for example, an IP address, a MAC address, an EHA address, a hardware address, an adapter address, or a physical address.

The computer network 10 can be connected to a network 155. The network 155 can include a private, public (e.g., the Internet), corporate, campus, government, hospital or any other computer network. The network 155 can include a satellite, a telecommunication network, or a system of networks.

The network security system 100 includes a plurality of computing resources 110 to 160. The network security system 100 can include a server farm 110, one or more switching and distribution layers 120, one or more routers 130, one or more network switches 140, a communication server 150, and a security appliance 160, all of which can be interconnected by communication links. The network security system 100 can include a firewall (not shown) that can shield the computing resources or nodes N in the computer network 10 from cyberattacks. The network security system 100 can facilitate communication between a communicating device 142 and another communication device 142 located in the computer network 10 or outside of the computer network 10, such as, for example, a communicating device (not shown) connected to the network 155.

The server farm 110 can include a plurality of computing resources, including, for example, a mail server 111, a web server 113, a file server 115 and a communication server 117. The computing resources 111, 113, 115 or 117 can be located in an intranet or an extranet (not shown). The intranet or extranet can include all the foregoing computing resources, including the firewall to protect against threats and breach attempts made against any node N in the computer network 10. The server farm 110 can include large numbers of computing resources that are accessible to other computing resources in the computer network 10, including, for example, the communicating devices 142.

The switching and distribution layers 120 can include a core layer 122 and a distribution layer 124. The core layer 122 can include one or more layers of switching devices (not shown) that can connect the server farm 110 to the distribution layer 124. The distribution layer 124 can include one or more layers of switching devices (not shown) that can connect the core layer 122 to the one or more routers 130, the one or more network switches 140, the communication server 117, or the security appliance 160. The switching and distribution layers 120 can include one or more routers (not shown).

The router(s) 130 can be connected to the intranet (not shown), extranet (not shown), or the network 155 via one or more communication links. If a security scanning analysis is generated by a security analyzer (not shown) located outside of the computer network 10, such as, for example, on a software vendor server on the Internet, the security scanning analysis can be received via the router 130 or directly by the security appliance 160 via a communication link. The router(s) 130 can include a firewall (not shown). The network switch(es) 140 can be connected to the communicating devices 142 by one or more associated communication links. The network switch(es) 140 can include ethernet switches (not shown). Data packets can be securely transported between nodes N in the computer network 10, and between nodes N in the computer network 10 and nodes outside the computer network 10 (not shown).

The communication server 117 can include a standards-based computing device that can operate as, for example, a carrier-grade common platform for a wide range of communications applications and facilitate communication over, for example, the PSTN 155 or the PLMN (not shown). The communication server 117 can include Internet message handling services that transfer electronic mail messages between communicating device 142 in the computer network 10 with communicating devices (not shown) located outside the computer network 10.

The security appliance 160 can include hardware, firmware, or software that can perform security analysis, vulnerability detection and identification, vulnerability classification and prioritization, remediation plan generation, or vulnerability remediation. The security appliance 160 can include a server. The security appliance 160 can include a cyber-vulnerability remediator (CVR) 200.

Figure 3:
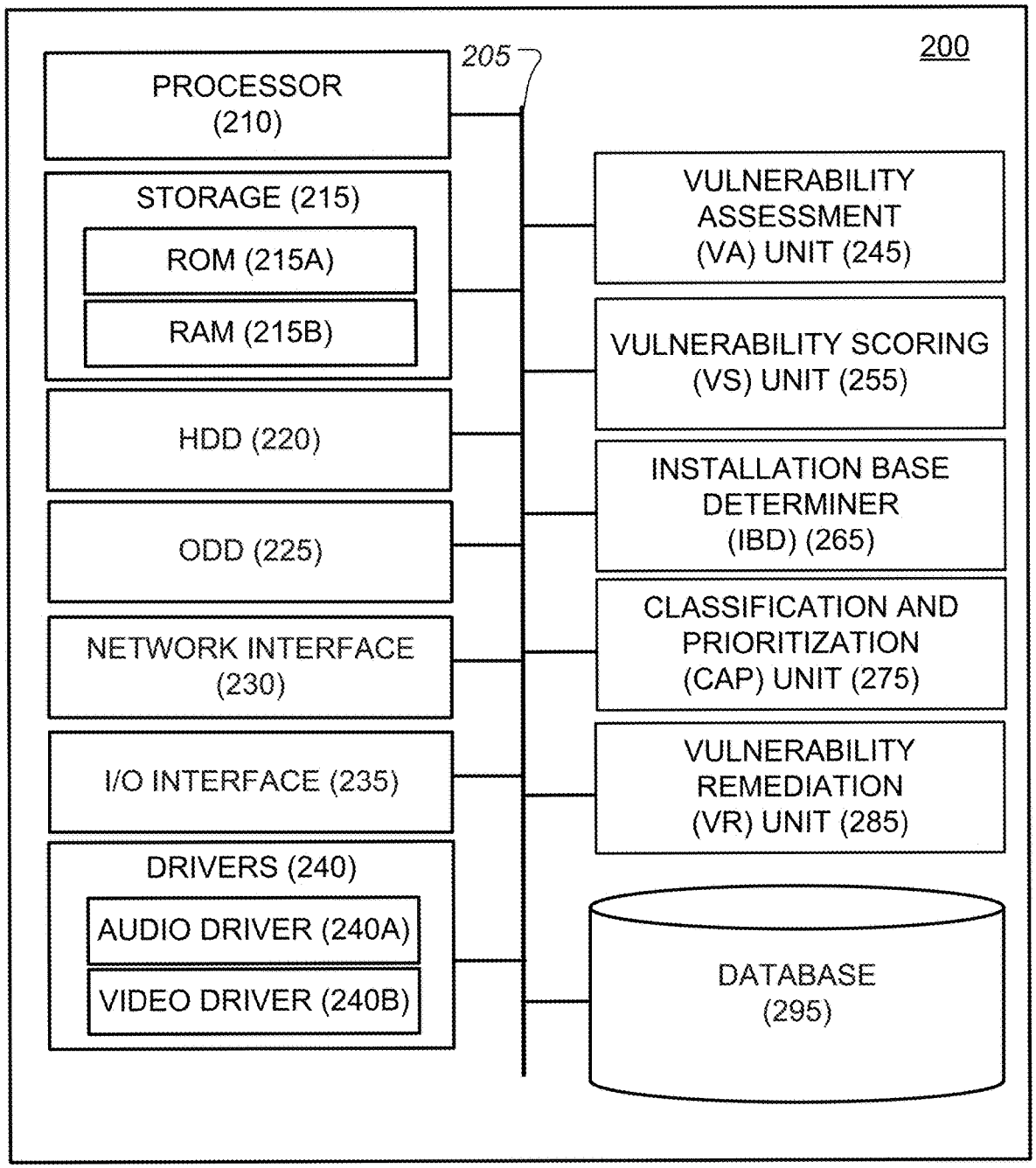
FIG. 3 shows an example of a cyber-vulnerability remediator (CVR) that can be included in the network security solution.

FIG. 3 shows a non-limiting embodiment of the cyber-vulnerability remediator (CVR) 200, constructed according to the principles of the disclosure. The CVR 200 can be configured to implement the various aspects of the disclosure. The CVR 200 can include a processor 210, a storage 215, a hard disk drive (HDD) 220, an optical disk drive (ODD) 225, a network interface 230, an input/output (I/O) interface 235, drivers 240, a vulnerability assessment (VA) unit 245, a vulnerability scoring (VS) unit 255, an installation base determiner (IBD) 265, a classification and prioritization (CAP) unit 275, a vulnerability remediation (VR) unit 285, a database 295, and a system bus 205, which can be communicatively linked to each of the computing resources 210-295 in the CVR 200 by a communication link. Any one or more of the computing resources 215 to 295 (including, for example, the VA unit 245, VS unit 255, IBD 265, CAP unit 275, or VR unit 285) can be a device or a module that is separate from the processor 210, as seen in FIG. 3, or integrated with the processor 210.

The system bus 205 can include any of several types of bus structures that can further interconnect to a memory bus (with or without a memory controller), a peripheral bus, and a local bus using any of a variety of commercially available bus architectures.

The processor 210 can include any of various commercially available processors. Dual microprocessors and other multi-processor architectures can also be employed as the processor. The processor 210 can include a central processing unit (CPU) or a graphic processing unit (GPU).

The CVR 200 can include a computer-readable medium that can hold executable or interpretable computer code (or instructions) that, when executed by the processor 210, causes the steps, processes and methods in this disclosure to be carried out. The computer-readable medium can be provided in the storage 215, HDD 220, or ODD 225. The computer readable medium can include sections of computer code that, when executed cause the CVR 200 to carry out a vulnerability assessment and remediation process 500 shown in FIG. 11, as well as all other process steps described or contemplated in this disclosure.

The storage 215 can include a read only memory (ROM) 215A and a random-access memory (RAM) 215B. The storage 215 can store vulnerability data. A basic input/output system (BIOS) can be stored in the non-volatile memory 215A, which can include, for example, a ROM, an EPROM, an EEPROM, or the like. The BIOS can contain the basic routines that help to transfer information between components within the CVR 200, such as during start-up. The RAM 215B can include a high-speed RAM such as static RAM for caching data.

The HDD 220 can include, for example, an enhanced integrated drive electronics (EIDE) drive, a serial advanced technology attachments (SATA) drive, or the like; and, the ODD 225 can read/write from/to a CD-ROM disk (not shown), or, read from or write to other high capacity optical media such as the DVD. The HDD 220 can be configured for external use in a suitable chassis (not shown). The HDD 220 and ODD 225 can be connected to the system bus 205 by a hard disk drive interface (not shown) and an optical drive interface (not shown), respectively. The hard disk drive interface (not shown) can include a Universal Serial Bus (USB) (not shown), an IEEE 1394 interface (not shown), and the like, for external applications.

The HDD 220 or ODD 225, and their associated computer-readable media, can provide nonvolatile storage of data, data structures, computer-executable instructions, and the like. The HDD 220 or ODD 225 can accommodate the storage of any data in a suitable digital format. The storage 215, HDD 220, or ODD 225 can include one or more apps that are used to execute aspects of the architecture described herein.

A number of program modules can be stored in the storage 215, HDD 220, or ODD 225, including an operating system (not shown), one or more application programs (not shown), other program modules (not shown), and program data (not shown). Any (or all) of the operating system, application programs, program modules, and program data can be cached in the RAM 215B as executable sections of computer code.

The network interface 230 can be connected to the network 155 (shown in FIG. 2). The network interface 230 can include a wired or a wireless communication network interface (not shown) or a modem (not shown). When used in a local area network (LAN), the CVR 200 can be connected to the LAN network (e.g., computer network 10 or network 155, shown in FIG. 2) through the wired or wireless communication network interface; and, when used in a wide area network (WAN), the CVR 200 can be connected to the WAN network through the modem. The computer network 10 or network 155 (shown in FIG. 2) can include a LAN, a WAN, or any other network. The modem (not shown) can be internal or external and wired or wireless. The modem can be connected to the system bus 205 via, for example, a serial port interface (not shown).

The (I/O) interface 235 can receive commands and data from an operator via the I/O interface, which can be communicatively coupled to one or more input/output devices (not shown), including, for example, a keyboard (not shown), a mouse (not shown), a pointer (not shown), a microphone (not shown), a speaker (not shown), or a display (not shown). The received commands and data can be forwarded from the I/O interface 235 as instruction and data signals via the bus 205 to any of the components in the CVR 200, including, for example, the processor 210, drivers 240, VA unit 245, VS unit 255, IBD 265, CAP unit 275, VR unit 285 or database 295.

The drivers 240 can include an audio driver 240A and a video driver 240B. The audio driver 240A can include a sound card, a sound driver (not shown), an interactive voice response (IVR) unit, or any other device necessary to render a sound signal on a sound production device (not shown), such as for example, a speaker (not shown). The video driver 240B can include a video card (not shown), a graphics driver (not shown), a video adaptor (not shown), or any other device necessary to render an image signal on a display device (not shown).

The VA unit 245 can include one or more vulnerability security analyzers that can detect, identify or assess vulnerabilities across many disparate hardware, firmware or software platforms. The security analyzer(s) can include, for example, Static Application Security Testing (SAST) tools, Dynamic Application Security Testing (DAST) tools, Software Composition Analysis (SCA) tools, Database Security Scanning (DSS) tools, Mobile Application Security Testing (MAST) tools, Interactive Application Security Testing (IAST) tools, Application Security Testing as a Service (ASTaaS) tools, Correlation tools, Test Coverage Analyzer tools, Application Security Testing Orchestration (ASTO) tools, logging and monitoring tools, log management tools, among many other tools that can analyze computing resources and detect, identify or assess vulnerabilities in the computing resources, as well as traffic received by or passing through the computing resources. The VA unit 245 can carry out penetration testing at each node N in the computer network 10. The VA unit 245 can check the computing resources in the computer network 10 against vulnerabilities available in public vulnerabilities directories like, for example, Common Vulnerabilities and Exposures (CVE), or focus on the different steps that an attacker might follow in order to perform an attack on a computing resource. The VA unit 245 can use substantially the same discovery and information gathering techniques that might be used by an attacker.

The VA unit 245 can scan or analyze each computing resource or vulnerability and sort the vulnerabilities according to, for example, the Open Web Application Security Project (OWASP) top 10 vulnerabilities in web applications criteria, including, for example, (A1) injection, (A2) broken authentication, (A3) sensitive data exposure, (A4) XML external entities (XXE), (A5) broken access control, (A6) security misconfiguration, (A7) cross-site scripting (XSS), (A8) insecure deserialization, (A9) using components with known vulnerabilities, and (A10) insufficient logging and monitoring. An OWASP listing of criteria that can be included can be found at, for example, <www.owasp.org>, including a brief description and explanation of each criteria. After analyzing and sorting the vulnerabilities, the vulnerability assessment unit 245 can output the vulnerability scanning results as vulnerability data. The vulnerability data can include information about each node N (e.g., node location identifier, last security scan date, platform type) and the computing resources installed or operating at the node N (e.g., identification, last security scan date, type, platform type). An aggregate of vulnerability data for the computer network 10 can facilitate determination of the criticality of each computing resource based on the number of installations in the computer network 10.

The security scanning analysis can be initiated or carried out by the VA unit 245 and can include a security scan result for each computing resource or vulnerability detected in a computing resource in the computer network 10 (shown in FIGS. 1 and 2). The security scanning analysis can be carried out for every node N in the computer network 10, including all computing resources at the nodes. Where a single node N includes a plurality of computing resources, such as, for example, the communicating device 142 (shown in FIG. 2), which can include hundreds or thousands of software applications, each computing resource at the node N can be scanned or analyzed. The VA unit 245 can generate an infrastructure vulnerabilities report for the computer network 10, including all actual or potential attack vectors, vulnerabilities or threats. The vulnerabilities report can be included in the vulnerability data generated and output by the VA unit 245, which can be included in a file-based form, or any other form that can facilitate analysis and review of the security scan results in the CVR 200.

According to an alternative embodiment, the VA unit 245 can be configured to receive vulnerability data from security scanning analysis tools located external to the CVR 200. For instance, one or more security analysis tools can be located outside the CVR 200 at one or more nodes N in the computer network 10, or outside the computer network 10 such as, for example, in a cloud network or a vendor server (not shown). In such instances, the vulnerability data can be received by the CVR 200 via the network interface 230 or I/O interface 235.

FIG. 4 shows an example of a vulnerability scanning summary matrix 300A that can be generated and populated with, for example, data parsed from the vulnerability data. The vulnerability scanning summary matrix 300A can include vulnerability data for each vulnerability or computing resource in the computer network 10 (shown in FIGS. 1 and 2). The vulnerability scanning summary matrix 300A can be populated with vulnerability data generated by the VA unit 245 or received from an external source (not shown) such as, for example, a security analyzer located outside the CVR 200. The vulnerability scanning summary matrix 300A can include a list of vulnerabilities and computing resources discovered or identified at each node N in the computer network 10.

The vulnerability scanning summary matrix 300A can include a computing resource identification field 310 and a vulnerability identification field 320. The computing resource identification field 310 can be populated with computing resource identification $CR_i$ data that can be parsed from the vulnerability data and used to identify each unique computing resource that is installed or operating in the computer network 10. The computing resource identification CR, can include, for example, a name of a computer program or application that is installed or operating in the computer network 10. In the non-limiting example shown in FIG. 4, the computing resource identification $CR_i$ data includes the computing resources Word®, Photoshop®, Acrobat®, CutPro®, and iExplore®.

The vulnerability identification field 320 can include a vulnerability identification for the vulnerability in the computing resource $CR_i$. The vulnerability identification field 320 can include vulnerability identification data, such as, for example, a Common Vulnerability and Exposures (CVE) identification number for the vulnerability in the computing resource $CR_i$ (e.g., CVE-42556, 54889, 63578, 56894, or 94546), or any other identifier that can identify the particular vulnerability in the computing resource $CR_i$. Based on the information in the computing resource identification field 310, each instance of a computing resource $CR_i$ installed or operating in the computer network 10 can be determined by, for example, the IBD 265, which can determine the total number of instances $N_{CRi}$ that each computing resource $CR_i$ is installed or operating in the computer network 10.

The VS unit 255 can include a vulnerability scoring system. The VS unit 255 can include, for example, CVSS, Common Weakness Enumeration (CWE), CVE, Common Attack Pattern Enumeration and Classification (CAPEC) or any compliance-oriented scheme appropriate for the computer network 10 that can classify, prioritize or score vulnerability in the network. Vulnerability data received from the VA unit 245 can be analyzed by the VS unit 255 to classify, rank, or score vulnerabilities in the computer network 10. The vulnerability data can be received by the VS unit 255 in a file-based form or any other form that facilitates classification, prioritization or scoring of the vulnerability scanning results by the VS unit 255. The VS unit 255 can include, for example, the vulnerability scoring unit 270 described in commonly owned U.S. patent application Ser. No. 16/196,544, filed Nov. 28, 2018, which is incorporated in this disclosure in its entirety by this reference.

According to an alternative embodiment, the VS unit 255 can receive vulnerability scoring data (including, for example, classification, prioritization or scoring data) from a vulnerability scoring tool (e.g., CVSS) located external to the CVR 200, such as, for example, at one or more nodes N in the computer network 10, or outside the computer network 10. The vulnerability scoring data can be received by the CVR 200 via the network interface 230 or I/O interface 235.

FIG. 5 shows an example of a vulnerability score summary matrix 300B that can be generated and populated with vulnerability scoring data. The vulnerability score summary matrix 300B can be populated with vulnerability scoring data generated by the VS unit 255 or can be received from the external vulnerability scoring tool (e.g., CVSS). The vulnerability score summary matrix 300B can include a vulnerability score field 330 and a severity level field 340. The vulnerability score field 330 can include CVSS score data, or scoring data from another compliance-oriented scheme, for each vulnerability identified in the vulnerability identification field 320 (shown in FIG. 4). The severity level field 340 can include severity level (or criticality) ratings, such, as, for example, low, medium, or high. The VS unit 255 can assign criticality ratings to discrete bands of vulnerability scores.

According to a non-limiting example, the VS unit 255 can assign a criticality rating of "LOW" (or 0) for CVSS scores between 0 and 3, "MEDIUM" (or 1) for CVSS scores between 4 and 6, and "HIGH" (or 2) for CVSS scores between 7 and 10. Additional criticality ratings and discrete bands of vulnerability scores are contemplated, including discrete subsets of each of the three criticality rating bands (e.g., CVSS scores 0-3, 4-6, and 7-10), such as, for example, a "HIGH-HIGH" for CVSS scores 9.0 or greater, "HIGH-MEDIUM" for CVSS scores between 8.0 and 9.0 and "HIGH-LOW" for CVSS scores between 7.0 and 8.0. The MEDIUM and LOW bands can similarly be divided into three discrete sub-bands for each (e.g., MEDIUM-HIGH, MEDIUM-MEDIUM, MEDIUM-LOW, LOW-HIGH, LOW-MEDIUM, LOW-LOW).

As seen in the example shown in FIG. 5, the VS unit 255 can assign a criticality rating of "LOW" for a CVSS score of 2, "MEDIUM" for CVSS scores of 5 and 6, and "HIGH" for CVSS scores of 7 and 7.5.

FIG. 6 shows an example of a vulnerability classification summary matrix 300C that can be generated and populated with vulnerability data or vulnerability scoring data. The vulnerability classification summary matrix 300C can be populated with vulnerability data and vulnerability scoring data generated by the CVR 200 (shown in FIG. 3). The vulnerability classification summary matrix 300C can include the computing resource identification ($CR_i$) field 310, vulnerability identification field 320, vulnerability score field 330, and severity level field 340 for all (or a subset of all) computing resources and vulnerabilities in the computer network 10 (shown in FIGS. 1 and 2). The vulnerability classification summary matrix 300C can be generated by, for example, the VS unit 255 or the processor 210 (shown in FIG. 3).

While common vulnerability scores and associated criticality ratings can facilitate prioritization and classification of vulnerabilities and computing resources based on risks associated with the vulnerabilities and computing resources, this approach by itself may not provide satisfactory results for large computer networks in real-world conditions and can generate ambiguous results that do not reflect the true risks associated with vulnerabilities in the computer networks. This disadvantage can result in erroneous prioritization and remediation of non-critical or less critical vulnerabilities at the expense of forgoing remediation of truly critical vulnerabilities in computer network where factors such as time or computing power might be restricted. For example, this can happen where a truly critical vulnerability (e.g., a vulnerability in a software application that is included at every node in the computer network) is assigned a "LOW" severity level (or criticality rating) and is not remediated because many other vulnerabilities are assigned "HIGH" criticality ratings and there are insufficient resources to address vulnerabilities having "LOW" criticality ratings. The erroneous prioritization and remediation can leave, for example, the most commonly installed software applications (e.g., search engines, spreadsheet tools, or application program interfaces (APIs)) in the computer network 10 to remain unremediated, thereby exposing the computer network 10 to a heightened risk of successful cyberattacks that can potentially severely impact or cripple the entire computer network 10. Widely installed computing resources (e.g., end-user software) with identified security weaknesses will have higher risk of exploitation in comparison to the less installed ones, since they present a bigger attack surface.

The IBD 265 or CAP unit 275 in the CVR 200 provide a technological solution that addresses these disadvantages and facilitates efficient and effective prioritization and remediation of vulnerabilities to ensure vulnerabilities in the computer network 10 are timely identified and remediated according to their true (or real-world) severity level.

The CAP unit 275 can reclassify and reprioritize vulnerabilities based on installation base data for the computer network 10, which can be parsed by the CAP unit 275 to classify, prioritize or score the vulnerabilities according to the true risks associated with those vulnerabilities, so that remediation can be carried out efficiently, accurately, and effectively. The CAP unit 275 can receive the installation base data from the IBD 265 and classify, prioritize or score each vulnerability in the computer network 10 for remediation according to the percentile of occurrence $PO_{CRi}$ for the associated computing resource $CR_i$. The CAP unit 275 can receive vulnerability score data from the VS unit 255 and reclassify, reprioritize or rescore the vulnerabilities or computing resources identified in the vulnerability score data. The CAP unit 275 can generate true severity level ratings for each vulnerability or computing resource $CR_i$ based on a percentile of occurrence $PO_{CRi}$ of the computing resource $CR_i$ in the computer network 10.

The IBD 265 can receive the vulnerability data (e.g., vulnerability data used to populate the vulnerability scanning summary matrix 300A shown in FIG. 4), including, for example, computing resource identification $CR_i$ data for each computing resource or node N in the computer network 10. The received vulnerability data can include $CR_i$ identification data for every (or less than all) computing resource in the computer network 10. The vulnerability data can be received from, for example, the VA unit 245 or an external source (not shown), such as, for example, a security analyzer or vulnerability scanner, via the network interface 230.

The IBD 265 can receive vulnerability score data (e.g., vulnerability score data used to populate the vulnerability scoring summary matrix 300B, shown in FIG. 5) from, for example, the VS unit 255. The vulnerability score data can include, for example, a vulnerability score for each vulnerability or computing resource or node in the computer network 10. The received vulnerability score data can include a vulnerability score for each vulnerability or computing resource at each node N or the entire computer network 10. The vulnerability score data can be received from an external source (not shown), such as, for example, a CVSS tool (not shown) located in the computer network 10, but external to the CVR 200, in which case it can be received via the network interface 230.

The IBD 265 can include computing resource installation base data for the computer network 10, or the computing resource installation base data can be received from the database 295 (shown in FIG. 3) or from a data source (not shown), such as, for example, a software development tool, an information security management system, a network log, an information technology (IT) inventory audit, or any other source that can provide information about the computing resources that are included, installed or operating at each node N in the computer network 10. The IBD 265 can receive the computing resource installation base data via, for example, the network interface 230 (shown in FIG. 3). The computing resource installation base data can include, for example, a directory of all nodes N in the computer network 10, as well as a directory of all computing resources installed at each node N.

The IBD 265 can determine a total number $N_{CRi}$ of each computing resource $CR_i$ that are installed or operating in the computer network 10, where i represents a unique computing resource. The total number $N_{CRi}$ of computing resources $CR_i$ can be determined by, for example, adding the total number of nodes N that include or operate the computing resource $CR_i$. The determination can be made by the IBD 265 based on, for example, the received vulnerability data or computing resource installation base data.

The percentile of occurrence $PO_{CRi}$ of a computing resource $CR_i$ in the computer network 10 can be determined according to the following equation (1):

$$PO_{CRi}=(N_{CRi}/n)\times 100 \qquad (1)$$

where n is the total number of nodes N in the computer network 10.

FIG. 7 shows an example of a vulnerability-installation-base (VIB) classification summary matrix 300D that can be generated and populated with total number of instances $N_{CRi}$ data. The VIB classification summary matrix 300D can be generated by the processor 210, IBD 265, or CAP unit 275. The VIB classification summary matrix 300D can be populated with VIB classification summary matrix data generated by the IBD 265 based on data received from the VA unit 245 and VS unit 255, or by the processor 210 or CAP unit 275 based on data received from the VA unit 245, VS unit 255, and IBD 265 (shown in FIG. 3).

The VIB classification summary matrix 300D can include a total number of instances $N_{CRi}$ field 350, in addition to the computing resource identification $CR_i$ field 310, vulnerability identification field 320, vulnerability score field 330, or severity level field 340. For each unique computing resource identified in the $CR_i$ field 310, the $N_{CRi}$ field 350 can include the total number of nodes N in the computer network 10 that include the computing resource $CR_i$.

In the non-limiting example shown in FIG. 7, the computer network 10 has 50,000 nodes N that have Word® installed ($CR_1$=Word®, $N_{CR1}$=50,000), 3,000 nodes N with Photoshop® ($CR_2$=Photoshop®, $N_{CR2}$=3,000), 30,000 nodes N with Acrobat® ($CR_3$=Acrobat®, $N_{CR3}$=30,000), 1,000 nodes N with CutPro® ($CRD_4$=CutPro®, $N_{CR4}$=1,000), and 45,000 nodes with iExplore® ($CR_5$=iExplore®, $N_{CR5}$=45,000). Assuming for purposes of this example that the computer network 10 has a total of 55,000 nodes N (i.e., n=55,000), the percentile of occurrence $PO_{CRi}$ for Word® is 90.9% ($PO_{CR1}$=($N_{CR1}$/n)×100). The percentile of occurrence $PO_{CRi}$ for each of the other computing resources (i.e., Photoshop®, Acrobat®, CutPro®, iExplore®) can be similarly determined.

The CAP unit 275 can receive the vulnerability installation base (VIB) data (e.g., data used to populate VIB classification summary matrix 300D, shown in FIG. 7) from the IBD 265. Alternatively, the CAP unit 275 can receive the vulnerability data (e.g., data in vulnerability scanning summary matrix 300A, shown in FIG. 4) from the VA unit 245, the vulnerability score data (e.g., data in vulnerability scoring summary matrix 300B, shown in FIG. 5) from the VS unit 255, and the total number $N_{CRi}$ data from the IBD 265. Based on the VIB data, the CAP unit 275 can prioritize, rank and score the vulnerabilities in the computer network 10 according to their true severity levels by applying a severity quantifier matrix (e.g, 400A shown in FIG. 8) and a severity adjustment matrix (e.g., 400B shown in FIG. 9).

FIG. 8 shows an example of a severity quantifier matrix 400A, which includes four discrete bands of ranking thresholds that can be applied to classify or rank the vulnerabilities in the computer network 10 based on the percentile of occurrence $PO_{CRi}$ of each computing resource $CR_i$ in the network. The severity quantifier matrix 400A can facilitate determination of the criticality of vulnerabilities or computing resources based on the number of installations of the computing resources in the network 10 divided into percentile groups. The percentile of occurrence $PO_{CRi}$ can be ranked from the lowest number of occurrences to the highest number of occurrences of a computing resource in the network. The four ranking thresholds can be set to, for example, a "Low" ranking threshold for computing resources that are installed in 0% to 10% of the total number n of nodes N in the network 10; a "Medium" ranking threshold for computing resources that are installed in 10% to 50% of the total number n of nodes N; a "High" ranking threshold for computing resources that are installed in 50% to 80% of the total number n of nodes N; and a "Critical" ranking threshold for computing resources that are installed in 80% to 100% of the total number n of nodes N in the network 10. After the ranking thresholds are determined for each of the vulnerabilities or computing resources, the CAP unit 275 can determine the severity level adjustment matrix for the vulnerabilities in the network 10.

FIG. 9 shows an example of a severity adjustment matrix 400B that can be generated by the CAP unit 275 (shown in FIG. 3). The severity adjustment matrix 400B can be applied to, for example, the vulnerability classification summary matrix (e.g., matrix 300C, shown in FIG. 6) to classify and rank vulnerabilities in the computer network 10 based on the installation base for the network 10. The severity adjustment matrix 400B can include the ranking thresholds in the severity quantifier matrix 400A (shown in FIG. 8). The severity adjustment matrix 400B can include one or more columns and one or more rows. Each column (or row) can include a range of percentile of occurrence ($\Delta PO_{CR}$) (e.g., 4 columns, including $\Delta PO_{CRi}$=80% to 100% band, 50% to 80% band, 10% to 50% band, 1% to 10% band) Each row (or column) can include a criticality rating (e.g., 4 rows, including Critical severity level, High severity level, Medium severity level, Low severity level). The severity adjustment matrix 400B can include a risk adjustment weight for each column-row cell. In the example shown in FIG. 9, the severity adjustment matrix 400B can be referenced by the CAP unit 275 to analyze and adjust the classification or ranking of vulnerabilities in the computer network 10.

Referring to FIGS. 6 and 9, the CAP unit 275 can reference the severity adjustment matrix 400B and adjust the classification and ranking values for the vulnerabilities in the vulnerability classification summary matrix 300C. For computing resources that are determined to be in the highest range of percentile of occurrence (e.g., $\Delta PO_{CR=80}$% to 100%), the value can be left unchanged for severity levels classified as "Critical" and increased to "Critical" for all other values of severity level (e.g., "High," "Medium," "Low"). Computing resources that are determined to be in the next range of percentile of occurrence (e.g., $\Delta PO_{CR}$=50% to 80%), the value can be left unchanged for severity levels classified as "Critical" or "High," and increased to a "High" for all other values of severity level (e.g., "Medium," "Low"). Computing resources that are determined to be in the third range of percentile of occurrence (e.g., $\Delta PO_{CR}$=10% to 50%), the value can be left unchanged for severity levels classified as "Critical," "High," or "Medium," and increased to "Medium" for all other values of severity level (e.g., "Low"). Computing resources that are determined to be in the lowest range of percentile of occurrence (e.g., $\Delta PO_{CR}$=1% to 10%), the value can be left unchanged.

FIG. 10 shows an example of a weighted vulnerability classification summary matrix 400C that can be generated and populated by the CAP unit 275 (shown in FIG. 3) for the vulnerabilities in the vulnerability classification summary matrix 300C (shown in FIG. 6). The weighted vulnerability classification summary matrix 400C can include a percentage field 360 and a true severity level field 370. The fields 360 and 370 can be in addition to one or more of the fields 310 to 350. In this example, values for the true severity level field 370 can be determined by applying the severity adjustment matrix 400B (shown in FIG. 9) to the values in the severity field 340.

In the examples shown in FIGS. 9 and 10, the severity level values of "High" and "Low" for $CR_1$=Word® and $CR_5$=iExplore®, respectively, is changed to "Critical" in both instances, since the software applications are installed at about 91% and about 82%, respectively, of the 55,000 nodes in the computer network 10. Meanwhile, the severity level values for Photoshop® ($CR_2$=Photoshop®) and Cut-Pro® ($CR_4$=CutPro®) are left unchanged. As seen in the examples, the vulnerabilities of the most widely installed or operated computing resources in the computer network 10 can be reclassified and reprioritized to the highest criticality ratings. As evident from the examples, the network security solution disclosed herein improves timely remediation, remediation effectiveness, and efficiency, allowing for vulnerability assessment and remediation of large numbers of computing resources with limited available resources.

The VR unit 285 can apply remediation to the vulnerabilities in the computer network 10 based on the weighted vulnerability classification summary matrix data (e.g., weighted vulnerability classification summary matrix 400C, shown in FIG. 10). The VR unit 285 can include a machine learning model such as, for example, an artificial neural network (ANN), a convolutional neural network (CNN), a recurrent neural network (RNN), a neural Turing machine (NTM), a differential neural computer (DNC), a support vector machine (SVM), or a deep learning neural network (DLNN). The VR unit 285 can generate or select vulnerability remediation solutions for each vulnerability. Alternatively, the VR unit 285 can send vulnerability data and weighted vulnerability classification summary matrix data (e.g., data used to populate the matrix 400C, shown in FIG. 10) to a communicating device 142 (shown in FIG. 2), which can be interacted with by, for example, a security analyst to investigate and resolve the associated vulnerability.

The database 295 can store vulnerability records for each node N and computing resource $CR_i$ in the computer network 10. The vulnerability records can include information for each node N and the computing resources $CR_i$ installed at that node, including, for example, location identifier, node location identifier, platform type, software name, date of most recent security scan or analysis, results of security scan or analysis, date of most recent software patch, software patch version, and any other information about the node, computing resource or vulnerability that can be useful in identifying, assessing, classifying, rating, or remediating vulnerabilities in the computer network 10. The database 295 can include computing resource installation base data for each node N in the computer network 10, including: an identification $CR_i$ for each computing resource installed at the node; remediation actions executed or to be executed to remediate vulnerabilities in the computing resources; and percentile of occurrence $PO_{CRi}$ for each computing resource. The database 295 can include historical data that can be accessed and sent to train a machine learning model in the VR unit 285.

Referring to FIGS. 7-10, the database 295 can store data used to populate the fields in each of the matrices shown in the examples. For instance, the database 295 can store the data used to populate the computing resource identification $CR_i$ field 310, vulnerability identification field 320, vulnerability score field 330, severity level field 340, total number $N_{CRi}$ field 350, percentage field 360, and true severity level field 370. The database 295 can be accessed by one or more of the computing resources 210 to 285 in the CVR 200 (shown in FIG. 3). The database 295 can receive queries and, in response, retrieve specific records or portions of records based on the queries. The database 295 can include a database management system (DBMS) that can interact with the computing resources in the CVR 200, such as, for example, the processor 210, VA unit 245, VS unit 255, IDB 265, CAP unit 275 or VR unit 285. The DBMS can interact with computing resources outside of the CVR 200, including, for example, the communicating devices 142 (shown in FIG. 2). The database 295 can include relational databases.

Figure 11:
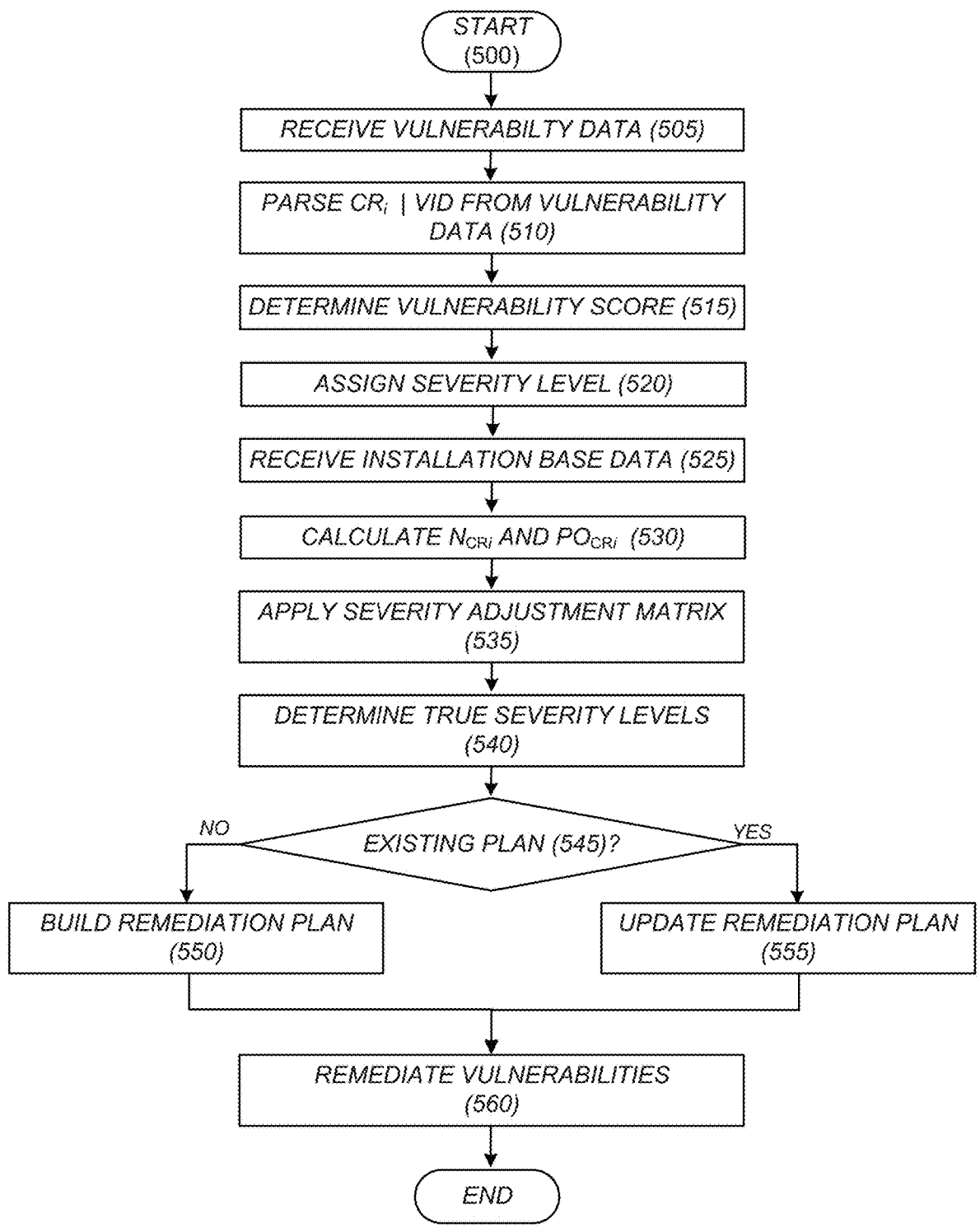
FIG. 11 shows an example of a vulnerability assessment and remediation process, according to the principles of the disclosure.

FIG. 11 shows an example of a vulnerability assessment and remediation process 500, according to the principles of the disclosure. The process 500 can be carried out by the CVR 200 (shown in FIG. 3). The CVR 200 can include or can access a computer readable medium that contains a computer program, which, when executed on one or more of computing devices, cause the process 500 to be carried out. The computer program can be tangibly embodied in the computer readable medium, comprising one or more program instructions, code segments, or code sections for performing each of the steps in the process 500 shown in FIG. 11, when executed by the one or more computing devices.

Referring to FIGS. 1-3 and 6-11, vulnerability data can be received for a plurality of computing resources $CR_i$ located in the computer network 10 (Step 505). The vulnerability data can be received for all, or less than all computing resources $CR_i$ in the network 10. In the example shown in FIGS. 6-7 and 10, vulnerability data can be received that includes a dataset having five computing resources $CR_1$ to $CR_5$, where $CR_1$=Word®, $CR_2$=Photoshop®, $CR_3$=Acrobat®, $CR_4$=CutPro®, $CR_5$=iExplore®. The vulnerability data can be received from, for example, the VA unit 245 (shown in FIG. 3), a security analyzer (not shown), or the database 295 (shown in FIG. 3). The received vulnerability data can include vulnerability scanning results for all (or less than all) vulnerabilities discovered or identified in the computing resources in the network 10. The security analyzer (not shown) can be located in the security appliance 160 (shown in FIG. 2) or elsewhere in the network 10, or it can be located at a third-party site that is external to network 10, such as, for example, at a vendor site. The security scan results can include vulnerability data for each node N in the network 10.

Computing resource identification $CR_i$ data and vulnerability identification (VID) data can be parsed from the vulnerability data (Step 510). FIG. 4 shows an example of the vulnerability scanning summary matrix 300A that can be populated with data parsed from the vulnerability data. The vulnerability data can be analyzed (e.g., by the VS unit 255, shown in FIG. 3) using, for example, at least one of basic metrics, temporal metrics, and environmental metrics as defined in the CVSS standard (e.g., CVSSv1.0, CVSSv2.0, or CVSSv3.0), to classify and rank the vulnerabilities and determine a vulnerability score (Step 515). The vulnerabilities can be prioritized according to classification and ranking, and a severity level can be assigned for each vulnerability (Step 520). FIG. 5 shows an example of the vulnerability score summary matrix 300B that can be populated with vulnerability scoring data and severity level data from the VS unit 255, or received from an external source (not shown) outside the CVR 200, such as, for example, a CVSS platform operating at one or more nodes N. Instead of, or in addition to the CVSS standard scoring scheme, any other vulnerability scoring scheme can be used that provides a repeatable, accurate score that can be implemented to classify and prioritize vulnerabilities based on their characteristics.

The vulnerability classification summary matrix 300C (shown in FIG. 6) can be generated and populated with the resource identification CR, data (field 310 in FIG. 6), VID data (field 320 n FIG. 6), vulnerability score data (field 330 in FIG. 6), and severity level data (field 340 in FIG. 6) for each computing resource $CR_1$ to $CR_5$ (e.g., $CR_1$=Word®, $CR_2$=Photoshop®, $CR_3$=Acrobat®, $CR_4$=CutPro®, $CR_5$=iExplore®, shown in FIG. 6).

Installation base data can be received for each of the computing resources $CR_i$ in the dataset with respect to the computer network 10 (e.g., $CR_1$=Word®, $CR_2$=Photoshop®, $CR_3$=Acrobat®, $CR_4$=CutPro®, $CR_5$=iExplore®, shown in FIG. 6) (Step 525). The computing resource installation base data can be determined by the IBD 265 (shown in FIG. 3) or received from the database 295 or the external information base data source (not shown).

A total number $N_{CRi}$ installations and percentiles of occurrence $PO_{CRi}$ in the computer network 10 can be calculated for each computing resource $CR_i$ in the dataset (Step 530). The calculation can be made based on the computing resource installation base data by adding the total number of nodes N that include or operate each computing resource $CR_i$ in the dataset to calculate the total number $N_{CRi}$ of installations (e.g., $N_{CR1}$=50,000, $N_{CR2}$=3,000, $N_{CR3}$=30,000, $N_{CR4}$=1,000, $N_{CR5}$=45,000 in FIG. 7) of each respective computing resource $CR_i$ in the network. The percentile of occurrence $PO_{CRi}$ (e.g., $PO_{CR1}$=91%, $PO_{CR2}$=5.45%, $PO_{CR3}$=31%, $PO_{CR4}$=1.81%, $PO_{CR5}$=81.81%) can be calculated for each computing resource $CR_i$ in the dataset by dividing the respective total number $N_{CRi}$ of installations for each computing resource $CR_i$ by the total number n of nodes in the network (e.g., n=55,000), according to equation (1).

After the percentiles of occurrence $PO_{CRi}$ are determined for all computing resources $CR_i$ in the dataset (e.g., $CR_1$ to $CR_5$) (Step 530), a severity adjustment matrix (e.g., 400B shown in FIG. 9) can be applied to the dataset (Step 535). The CAP unit 275 (shown in FIG. 3) can apply each of the values in the severity adjustment matrix 400B (shown in FIG. 9) to adjust the classification and ranking value for each of the computing resources $CR_i$ in the dataset and determine a true severity level for each computing resources $CR_i$ in the dataset (Step 540). A weighted vulnerability classification summary matrix 400C (shown in FIG. 10) can be generated for the dataset.

After true severity levels are determined for all computing resources $CR_i$ in the dataset (Step 540), a determination can be made whether a remediation plan exists for the computer network 10 (Step 545). If it is determined that a remediation plan does not exist (NO at Step 545), then a remediation plan can be built to resolve or remediate the vulnerabilities in the dataset (Step 550). However, if it is determined that a remediation plan exists for the computer network 10 (YES at Step 545), then the plan can be updated with the true severity levels and the vulnerabilities reclassified and reprioritized for remediation according to their true severity levels (Step 555).

The vulnerability remediation plan can be executed by the VR unit 285, or the vulnerability remediation plan can be transmitted to a communicating device 142 (shown in FIG. 2) that can apply the remediation plan to the vulnerabilities in the dataset (Step 560). Regarding the latter, the communicating device 142 can be located a security analyst location in the computer network 10.

The terms "a," "an," and "the," as used in this disclosure, means "one or more," unless expressly specified otherwise.

The term "communicating device," as used in this disclosure, means any hardware, firmware, or software that can transmit or receive data packets, instruction signals or data signals over a communication link. The hardware, firmware, or software can include, for example, a telephone, a smart phone, a satellite phone, a personal data assistant (PDA), a smart watch, a tablet, a computer, a software defined radio (SDR), a software defined transmitter or a software defined receiver. The communicating device can be portable or stationary.

The term "communication link," as used in this disclosure, means a wired or wireless medium that can convey data or information between at least two points. The wired or wireless medium can include, for example, a metallic conductor link, a radio frequency (RF) communication link, an Infrared (IR) communication link, an optical communication link, or a radiant energy link. The RF communication link can include, for example, WiFi, WiMAX, IEEE 802.11, DECT, 0G, 1G, 2G, 3G, 4G or 5G cellular standards, or Bluetooth.

The terms "computer" or "computing device," as used in this disclosure, means any machine, device, circuit, component, or module, or any system of machines, devices, circuits, components, or modules that are capable of manipulating data according to one or more instructions, such as, for example, without limitation, a processor, a microprocessor, a central processing unit, a graphic processing unit, a general purpose computer, a super computer, a personal computer, a laptop computer, a palmtop computer, a notebook computer, a desktop computer, a workstation computer, a server, a server farm, a computer cloud, or the like, or an array of processors, microprocessors, central processing units, general purpose computers, super computers, personal computers, laptop computers, palmtop computers, notebook computers, desktop computers, workstation computers, servers, or the like, without limitation.

The term "computing resource," as used in this disclosure, means a computing device, a communicating device, a communication link, software, a software application, a web application, a web page, a computer application, an application programming interface (API), a computer program, computer code, machine executable instructions, a storage device, firmware, or hardware. A computing resource can include any hardware, software, firmware or device that has or can be configured to have an Internet Protocol (IP) address, including, for example, a router, a switch, a server, a printer, a scanner, a camera, or an Internet-of-Things (IoT) device.

The term "computer readable medium," as used in this disclosure, means any non-transitory storage medium that participates in providing data (for example, instructions) that can be read by a computer. Such a medium can take many forms, including non-volatile media and volatile media. Non-volatile media can include, for example, optical or magnetic disks and other persistent memory. Volatile media can include dynamic random-access memory (DRAM). Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read. The computer-readable medium can include a "Cloud," which can include a distribution of files across multiple (e.g., thousands of) memory caches on multiple (e.g., thousands of) computers.

Various forms of computer readable media can be involved in carrying sequences of instructions to a computer. For example, sequences of instruction (i) can be delivered from a RAM to a processor, (ii) can be carried over a wireless transmission medium, or (iii) can be formatted according to numerous formats, standards or protocols, including, for example, WiFi, WiMAX, IEEE 802.11, DECT, 0G, 1G, 2G, 3G, 4G, or 5G cellular standards, or Bluetooth.

The term "database," as used in this disclosure, means any combination of software or hardware, including at least one application or at least one computer. The database can include a structured collection of records or data organized according to a database model, such as, for example, but not limited to at least one of a relational model, a hierarchical model, or a network model. The database can include a database management system application (DBMS). The at least one application can include, but is not limited to, for example, an application program that can accept connections to service requests from a destination communicating device by sending back responses to source communicating device(s). The database can be configured to run the at least one application, often under heavy workloads, unattended, for extended periods of time with minimal human direction.

The terms "including," "comprising" and variations thereof, as used in this disclosure, mean "including, but not limited to," unless expressly specified otherwise.

The term "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, a telecommunications network, or the Internet, any of which can be configured to communicate data via a wireless or a wired communication medium. These networks can run a variety of protocols not limited to TCP/IP, IRC or HTTP.

The term "node," as used in this disclosure, means a physical or virtual location in a computer network that comprises at least one computing resource.

The term "server," as used in this disclosure, means any combination of software or hardware, including at least one application or at least one computer to perform services for connected computing resources as part of a client-server architecture. The at least one server application can include, but is not limited to, for example, an application program that can accept connections to service requests from a communicating device by sending back responses to other communicating device(s). The server can be configured to run the at least one application, often under heavy workloads, unattended, for extended periods of time with minimal human direction. The server can include a plurality of computers configured, with the at least one application being divided among the computers depending upon the workload. For example, under light loading, the at least one application can run on a single computer. However, under heavy loading, multiple computers can be required to run the at least one application. The server, or any if its computers, can also be used as a workstation.

The term "transmission," as used in this disclosure, means the conveyance of signals via electricity, acoustic waves, light waves and other electromagnetic emissions, such as those generated with communications in the radio frequency (RF) or infrared (IR) spectra. Transmission media for such transmissions can include coaxial cables, copper wire and fiber optics, including the wires that comprise a system bus coupled to the processor.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential or a parallel order, such processes, methods and algorithms may be configured to work in alternate orders. In other words, any sequence or order of steps that may be described in a sequential order does not necessarily indicate a requirement that the steps be performed in that order; some steps may be performed simultaneously. Similarly, if a sequence or order of steps is described in a parallel (or simultaneous) order, such steps can be performed in a sequential order. The steps of the processes, methods or algorithms described herein may be performed in any order practical.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications, or modifications of the disclosure.

What is claimed is:

1. A method for remediating a cyberattack risk for a computing resource located at a node in a computer network having a plurality of nodes, the method comprising:
receiving vulnerability score data that includes a severity level for a vulnerability in the computing resource at said node;
receiving a number of installations value (NcRi) that indicates a number of instances the computing resource is included in the plurality of nodes;
determining a percentile of occurrence value (POrni) for the computing resource based on the number of installations value (Nrni);
generating a weighted vulnerability classification summary matrix having rows identifying computer resources, having a column indicating a severity level for each identified computer resource, and having a column indicating a true severity level for each identified computer resource;
applying a severity adjustment matrix to the severity level to determine the true severity level for the vulnerability in the computing resource in the weighted vulnerability classification summary matrix, wherein the severity adjustment matrix has columns indicating ranges of percentiles of occurrence, and has rows indicating severity ratings, and wherein the true severity level for each identified computer resource in the weighted vulnerability classification summary matrix is determined by the corresponding range of percentile and the severity rating of the respective identified computer resource;
reprioritizing the vulnerability in the computing resource based on the true severity level; and
mitigating the cyberattack risk for the computing resource based on the true severity level.

2. The method in claim 1, wherein the vulnerability score data comprises a Common Vulnerability Scoring System (CVSS) score for the vulnerability in the computing resource.

3. The method in claim 1, further comprising:
generating a remediation plan for the computer network.

4. The method in claim 3, wherein the generating the remediation plan comprises generating the weighted vulnerability classification summary matrix that includes the vulnerability in the computing resource.

5. The method in claim 1, wherein the computing resource comprises a software application.

6. The method in claim 1, wherein the determining the percentile of occurrence value (POrni) for the computing resource is calculated based on the number of installations value (NcRi) according to the equation $$POcRi=(NcRi/n) \times 100$$

where n is the total number of nodes in the computer network.

7. The method in claim 1, wherein the true severity level comprises a critical rating when the percentile of occurrence value (POcRi) for the computing resource is determined to be in a top percentile group.

8. The method in claim 1, further comprising:
generating the weighted vulnerability classification summary matrix that includes the vulnerability in the computing resource; and
transmitting the weighted vulnerability classification summary matrix to a communicating device in the computer network.

9. The method in claim 8, wherein the mitigating the cyberattack risk for the computing resource based on the true severity level is executed by the communicating device.

10. A non-transitory computer readable medium that stores instructions for remediating a cyberattack risk in a computing resource located at a node in a computer network having a plurality of nodes comprising machine executable code which when executed by at least one computing device, causes the at least one computing device to perform steps comprising:
receiving vulnerability score data that includes a severity level for a vulnerability in the computing resource at said node;
receiving a number of installations value (NcRi) that indicates a number of instances the computing resource is included in the plurality of nodes;
determining a percentile of occurrence value (POrni) for the computing resource based on the number of installations value (Nrni);
generating a weighted vulnerability classification summary matrix having rows identifying computer resources, having a column indicating a severity level for each identified computer resource, and having a column indicating a true severity level for each identified computer resource;
applying a severity adjustment matrix to the severity level to determine the true severity level for the vulnerability in the computing resource in the weighted vulnerability classification summary matrix, wherein the severity adjustment matrix has columns indicating ranges of percentiles of occurrence, and has rows indicating severity ratings, and wherein the true severity level for each identified computer resource in the weighted vulnerability classification summary matrix is determined by the corresponding range of percentile and the severity rating of the respective identified computer resource;
reprioritizing the vulnerability in the computing resource based on the true severity level; and
mitigating the cyberattack risk for the computing resource based on the true severity level.

11. The non-transitory computer readable medium in claim 10, wherein the vulnerability score data comprises a Common Vulnerability Scoring System (CVSS) score for the vulnerability in the computing resource.

12. The non-transitory computer readable medium of claim 10, the machine executable code further causing the at least one computing device to perform generating a remediation plan for the computer network.

13. The non-transitory computer readable medium in claim 10, the machine executable code further causing the at least one computing device to generate the weighted vulnerability classification summary matrix that includes the vulnerability in the computing resource.

14. The non-transitory computer readable medium in claim 10, wherein the computing resource comprises a software application.

15. The non-transitory computer readable medium in claim 10, wherein the percentile of occurrence value (POcRi) for the computing resource is calculated based on the number of installations value (NcRi) according to the equation $$POcRi=(NcRi/n) \times 100$$

where n is the total number of nodes in the computer network.

16. The non-transitory computer readable medium in claim 10, wherein the true severity level comprises a critical rating when the percentile of occurrence value (POrni) for the computing resource is determined to be in a top percentile group.

* * * * *